(12) United States Patent
Kwok et al.

(10) Patent No.: US 6,634,358 B2
(45) Date of Patent: *Oct. 21, 2003

(54) NASAL MASK CUSHION ASSEMBLY

(75) Inventors: Philip Rodney Kwok, West Pymble (AU); Robert Edward Styles, Glenhaven (AU)

(73) Assignee: ResMed Limited, North Ryde (AU)

(*) Notice: Subject to any disclaimer, the term of this patent is extended or adjusted under 35 U.S.C. 154(b) by 28 days.

This patent is subject to a terminal disclaimer.

(21) Appl. No.: 09/566,806

(22) Filed: May 8, 2000

(65) Prior Publication Data

US 2002/0005200 A1 Jan. 17, 2002

Related U.S. Application Data

(63) Continuation of application No. 08/791,212, filed on Jan. 31, 1997, now Pat. No. 6,112,746.

(30) Foreign Application Priority Data

Jul. 26, 1996 (AU) .............................................. PO1265

(51) Int. Cl.[7] .............................................. A62B 18/02
(52) U.S. Cl. .......................... 128/205.25; 128/206.24; 128/206.26; 128/207.13
(58) Field of Search ....................... 128/205.25, 206.24, 128/207.11

(56) References Cited

U.S. PATENT DOCUMENTS

| 781,516 A | 1/1905 | Guthrie |
| 812,706 A | 2/1906 | Warbasse |
| 1,081,745 A | 12/1913 | Johnston et al. |
| 1,105,127 A | 7/1914 | Drager .................. 128/206.26 |

(List continued on next page.)

FOREIGN PATENT DOCUMENTS

| AU | 64058/86 | 4/1987 |
| AU | 91/77110 B | 11/1991 |
| AU | 94/64816 B | 12/1994 |
| AU | 95/16178 B | 7/1995 |

(List continued on next page.)

OTHER PUBLICATIONS

"ResMed Sullivan Mirage—The Mirage is Real—A Perfect Fit—First Time," product brochure ®ResMed Limited 1997, 4 pages.
Mirage Spare Parts Brochure, 1997, 2 pages.
Mask 1 photographs, Respironics, Inc., Reusable Full mask (small) Part # 452033 lot # 951108.
Mask 2 Photographs, Puritain–Bennett, Adam Circuit, Shell part # 231700, Swivel part 190 616329–00, Pillows (medium) Part # 616324.

(List continued on next page.)

*Primary Examiner*—Aaron J. Lewis
(74) *Attorney, Agent, or Firm*—Pillsbury Winthrop LLP

(57) ABSTRACT

A nasal cushion (30) comprises a substantially triangularly shaped frame (32) from which extends a membrane (34). The frame (32) has a scalloped edge (36) by which the cushion (30) is affixed to a mask body. The membrane (34) has an aperture (38) into which the wearer's nose is received. The membrane (34) is spaced away from the rim (40) of the frame (32), and its outer surface (41) is of substantially the same shape as the rim (40). Respective notches (42,44) receive the bridge of the wearer's nose. The wearer's nose is received through the aperture (38) into the chamber within the mask body (46). The seal forming portion (45) thus contacts both the surface of the wearer's nose and a portion of the wearer's face in the region between the base of the nose and the upper lip, and around the sides and over the bridge of the nose. The shape of the seal forming portion (45) is particularly suited to effectively seal the difficult region of the facial contour that is the crease between the sides of the nose and the face.

130 Claims, 3 Drawing Sheets

U.S. PATENT DOCUMENTS

| | | | |
|---|---|---|---|
| 1,192,186 A | 7/1916 | Greene | |
| 1,206,045 A | 11/1916 | Smith | |
| 1,632,449 A | 6/1927 | McKesson | 128/206.24 |
| 1,653,572 A | 12/1927 | Jackson | |
| 1,926,027 A | 9/1933 | Biggs | |
| 2,123,353 A | 7/1938 | Catt | |
| 2,166,164 A | 7/1939 | Lemberg | |
| 2,248,477 A | 7/1941 | Lombard | |
| 2,254,854 A | 9/1941 | O'Connell | |
| 2,317,608 A | 4/1943 | Heidbrink | |
| 2,371,965 A | 3/1945 | Lemberg | |
| 2,376,871 A | 5/1945 | Fink | |
| 2,415,846 A | 2/1947 | Randall | |
| 2,438,058 A | 3/1948 | Kincheloe | |
| 2,465,973 A | 3/1949 | Bulbulian | |
| 2,578,621 A | 12/1951 | Yant | |
| 2,625,155 A | 1/1953 | Engelder | 128/206.24 |
| 2,875,757 A | 3/1959 | Galleher, Jr. | 128/206.26 |
| 2,931,356 A | 4/1960 | Schwarz | |
| D188,084 S | 5/1960 | Garelick | |
| 2,939,458 A | 6/1960 | Lundquist | |
| 3,013,556 A | 12/1961 | Galleher | |
| 3,044,464 A | 7/1962 | Gray | 128/205.25 |
| 3,182,659 A | 5/1965 | Blount et al. | |
| 3,189,027 A | 6/1965 | Bartlett | |
| 3,193,624 A | 7/1965 | Webb et al. | |
| 3,227,159 A | 1/1966 | Borgia et al. | |
| 3,238,943 A | 3/1966 | Holley | |
| 3,315,674 A | 4/1967 | Bloom et al. | |
| 3,330,273 A | 7/1967 | Bennett | |
| 3,330,274 A | 7/1967 | Bennett | 128/206.26 |
| 3,362,420 A | 1/1968 | Blackburn et al. | |
| 3,363,833 A | 1/1968 | Laerdal | |
| 3,521,630 A | 7/1970 | Westberg et al. | |
| 3,556,122 A | 1/1971 | Laerdal | |
| 3,580,051 A | 5/1971 | Blevins | |
| 3,680,555 A | 8/1972 | Warncke | |
| 3,700,000 A | 10/1972 | Hesse et al. | |
| 3,720,235 A | 3/1973 | Schrock | |
| 3,725,953 A | 4/1973 | Johnson et al. | 2/428 |
| 3,796,216 A | 3/1974 | Schwarz | |
| 3,799,164 A | 3/1974 | Rollins | |
| D231,803 S | 6/1974 | Huddy | |
| 4,077,404 A | 3/1978 | Elam | |
| D250,131 S | 10/1978 | Lewis et al. | |
| 4,167,185 A | 9/1979 | Lewis | |
| 4,174,710 A | 11/1979 | Pampuch | |
| 4,226,234 A | 10/1980 | Gunderson | |
| 4,245,632 A | 1/1981 | Houston | |
| D262,322 S | 12/1981 | Mizerak | |
| 4,304,229 A | 12/1981 | Curtin | |
| 4,305,387 A | 12/1981 | Reist-Kundig et al. | 128/202.28 |
| 4,328,797 A | 5/1982 | Rollins et al. | |
| 4,347,205 A | 8/1982 | Stewart | |
| 4,354,488 A | 10/1982 | Bartos | |
| 4,402,316 A | 9/1983 | Gadberry | |
| 4,412,537 A | 11/1983 | Tiger | |
| 4,414,973 A | 11/1983 | Matheson et al. | |
| 4,454,880 A | 6/1984 | Muto et al. | |
| 4,467,799 A | 8/1984 | Steinberg | |
| 4,522,639 A | 6/1985 | Ansite et al. | |
| 4,558,710 A | 12/1985 | Eichler | |
| 4,574,799 A | 3/1986 | Warncke | |
| 4,616,647 A | 10/1986 | McCreadie | |
| 4,622,964 A | 11/1986 | Flynn | |
| 4,655,213 A | 4/1987 | Rappaport et al. | |
| 4,665,570 A | 5/1987 | Davis | |
| 4,671,271 A | 6/1987 | Bishop et al. | |
| 4,677,975 A | 7/1987 | Edgar et al. | |
| 4,677,977 A | 7/1987 | Wilcox | |
| H397 H | 1/1988 | Stark | |
| D293,613 S | 1/1988 | Wingler | |
| 4,739,755 A | 4/1988 | White et al. | |
| 4,770,169 A | 9/1988 | Schmoegner et al. | |
| 4,774,941 A | 10/1988 | Cook | |
| 4,782,832 A | 11/1988 | Trimble et al. | |
| 4,794,921 A | 1/1989 | Lindkvist | |
| 4,799,477 A | 1/1989 | Lewis | |
| 4,803,981 A | 2/1989 | Vickery | |
| 4,809,692 A | 3/1989 | Nowacki et al. | |
| 4,811,730 A | 3/1989 | Milano | 128/203.11 |
| 4,819,629 A | 4/1989 | Jonson | |
| 4,821,713 A | 4/1989 | Bauman | |
| 4,841,953 A | 6/1989 | Dodrill | |
| 4,848,334 A | 7/1989 | Belim | |
| 4,848,366 A | 7/1989 | Alta et al. | |
| 4,907,584 A | 3/1990 | McGinnis | |
| 4,910,806 A | 3/1990 | Baker et al. | |
| 4,919,128 A | 4/1990 | Kopola et al. | |
| 4,922,921 A | 5/1990 | Donoghue | 600/530 |
| 4,938,210 A | 7/1990 | Shene | |
| 4,938,212 A | 7/1990 | Gnook et al. | |
| 4,944,310 A | 7/1990 | Sullivan | |
| D310,431 S | 9/1990 | Belim | |
| 4,971,051 A | 11/1990 | Toffolon | |
| 4,986,269 A | 1/1991 | Hakkinen | |
| 4,989,596 A | 2/1991 | Macris et al. | |
| 4,989,599 A | 2/1991 | Carter | |
| 5,003,633 A * | 4/1991 | Itoh | 128/206.24 |
| 5,005,568 A | 4/1991 | Loescher et al. | |
| 5,005,571 A | 4/1991 | Dietz | |
| 5,038,776 A | 8/1991 | Harrison et al. | |
| 5,042,473 A | 8/1991 | Lewis | |
| 5,042,478 A | 8/1991 | Kopala et al. | |
| 5,046,200 A | 9/1991 | Feder | |
| 5,063,922 A | 11/1991 | Hakkinen | |
| 5,069,205 A | 12/1991 | Urso | |
| D323,908 S | 2/1992 | Hollister et al. | |
| 5,109,839 A | 5/1992 | Blasdell et al. | |
| 5,109,840 A | 5/1992 | Daleiden | |
| 5,121,745 A | 6/1992 | Israel | |
| 5,133,347 A | 7/1992 | Huennenbeck | |
| 5,140,980 A | 8/1992 | Haughey et al. | |
| 5,140,982 A | 8/1992 | Bauman | |
| 5,148,802 A | 9/1992 | Sanders et al. | |
| 5,159,938 A | 11/1992 | Laughlin | |
| 5,178,138 A | 1/1993 | Walstrom et al. | |
| D334,633 S | 4/1993 | Rudolph | |
| 5,220,699 A | 6/1993 | Farris | |
| 5,231,983 A | 8/1993 | Matson et al. | |
| 5,233,978 A | 8/1993 | Callaway | |
| 5,243,971 A * | 9/1993 | Sullivan et al. | 128/207.13 |
| 5,265,595 A | 11/1993 | Rudolph | |
| 5,279,289 A | 1/1994 | Kirk | |
| 5,280,784 A | 1/1994 | Kohler | |
| 5,311,862 A | 5/1994 | Blasdell et al. | |
| 5,322,057 A | 6/1994 | Raabe et al. | |
| 5,343,878 A | 9/1994 | Scarberry et al. | |
| 5,349,949 A | 9/1994 | Schegerin | 128/206.24 |
| 5,357,951 A | 10/1994 | Ratner | |
| 5,372,130 A | 12/1994 | Stern et al. | |
| 5,388,571 A | 2/1995 | Roberts et al. | |
| 5,404,871 A | 4/1995 | Goodman et al. | |
| 5,419,318 A | 5/1995 | Tayebi | |
| 5,429,126 A | 7/1995 | Bracken | |
| 5,429,683 A | 7/1995 | Le Mitouard | |
| 5,431,158 A | 7/1995 | Tirotta | |
| 5,438,981 A | 8/1995 | Starr et al. | |
| 5,441,046 A * | 8/1995 | Starr et al. | 128/207.11 |
| D362,061 S | 9/1995 | McGinnis et al. | |
| 5,477,852 A | 12/1995 | Landis et al. | |

| | | | | | | |
|---|---|---|---|---|---|---|
| 5,479,920 A | 1/1996 | Piper et al. | | EP | 0 602 424 | 11/1993 |
| 5,488,948 A | 2/1996 | Dubruille et al. | | EP | 0 634 186 A2 | 6/1994 |
| 5,492,116 A | 2/1996 | Scarberry et al. | | EP | 0 608 684 A1 | 8/1994 |
| 5,501,214 A | 3/1996 | Sabo | | EP | 178 925 A2 | 4/1996 |
| 5,509,404 A | 4/1996 | Lloyd et al. | | EP | 0 747 078 | 12/1996 |
| 5,517,986 A | 5/1996 | Starr et al. | | EP | 0 747 078 A2 | 12/1996 |
| 5,538,000 A | 7/1996 | Rudolph | | EP | 0821 978 | 2/1998 |
| 5,540,223 A * | 7/1996 | Starr et al. ............ 128/206.24 | | FR | 801629 | 8/1936 |
| 5,542,128 A | 8/1996 | Lomas | | FR | 858749 | 12/1940 |
| 5,546,936 A | 8/1996 | Virag et al. | | FR | 2 254 657 A1 | 6/1986 |
| RE35,339 E | 10/1996 | Rappaport | | FR | 2 658 725 A1 | 8/1991 |
| 5,560,354 A * | 10/1996 | Berthon-Jones | | FR | 2 749 176 | 12/1997 |
| | | et al. ............... 128/206.24 | | GB | 775911 | 5/1957 |
| 5,570,682 A | 11/1996 | Johnson | | GB | 1395391 | 5/1975 |
| 5,570,689 A * | 11/1996 | Starr et al. ............ 128/206.24 | | GB | 1 467 828 | 3/1977 |
| D377,089 S | 12/1996 | Starr et al. | | GB | 2145335 A | 3/1985 |
| 5,592,938 A * | 1/1997 | Scarberry et al. ...... 128/206.24 | | GB | 2147506 A | 5/1985 |
| 5,608,647 A | 3/1997 | Rubsamen et al. | | GB | 2 164 569 A | 3/1986 |
| 5,642,730 A | 7/1997 | Baran | | GB | 2211098 A | 6/1989 |
| 5,647,355 A | 7/1997 | Starr et al. | | GB | 2 267 648 A | 12/1993 |
| 5,647,357 A | 7/1997 | Barnett et al. | | IT | 326983 | 6/1935 |
| 5,649,532 A | 7/1997 | Oren | | JP | 09/216240 A | 8/1997 |
| 5,649,533 A | 7/1997 | Griffiths | | WO | WO 80/01044 | 5/1980 |
| 5,655,520 A | 8/1997 | Howe et al. | | WO | WO 82/03548 | 10/1982 |
| 5,655,527 A | 8/1997 | Scarberry | | WO | WO 86/06969 | 12/1986 |
| 5,657,493 A | 8/1997 | Ferrero et al. | | WO | WO 87/01950 | 4/1987 |
| 5,657,752 A * | 8/1997 | Landis et al. .......... 128/207.13 | | WO | WO 91/03277 | 3/1991 |
| 5,660,174 A | 8/1997 | Jacobelli ............... 128/206.24 | | WO | WO 92/15353 | 9/1992 |
| 5,662,101 A * | 9/1997 | Ogden et al. .......... 128/206.24 | | WO | WP 92/20395 | 11/1992 |
| 5,666,946 A | 9/1997 | Langenback | | WO | WO 93/01854 | 2/1993 |
| 5,685,296 A | 11/1997 | Zdrojkowski et al. | | WO | WO 94/02190 | 2/1994 |
| 5,687,715 A | 11/1997 | Landis et al. | | WO | WO 94/16759 | 8/1994 |
| 5,715,814 A | 2/1998 | Ebers | | WO | WO 94/19055 | 9/1994 |
| 5,724,965 A | 3/1998 | Handke et al. | | WO | WO 94/20051 | 9/1994 |
| 5,746,201 A | 5/1998 | Kidd | | WO | WO 95/02428 | 1/1995 |
| 5,813,423 A | 9/1998 | Kirchgeorg | | WO | 0 697 225 | 7/1995 |
| 5,832,918 A | 11/1998 | Pantino | | WO | WO 96/17643 | 6/1996 |
| 5,884,624 A * | 3/1999 | Barnett et al. ......... 128/206.24 | | WO | WP 96/25983 | 8/1996 |
| 5,921,239 A | 7/1999 | McCall et al. | | WO | WO 96/39206 | 12/1996 |
| 6,082,360 A * | 7/2000 | Rudolph et al. ....... 128/206.24 | | WO | WO 97/07847 | 3/1997 |
| 6,102,040 A | 8/2000 | Tayebi et al. .......... 128/206.24 | | WO | WO 97/41911 | 11/1997 |
| 6,119,693 A | 9/2000 | Kwok et al. | | WO | WO 98/04310 | 2/1998 |
| 6,357,441 B1 | 3/2002 | Kwok et al. | | WO | WO 98/11930 | 3/1998 |
| | | | | WO | WO 98/18514 | 5/1998 |
| | FOREIGN PATENT DOCUMENTS | | | WO | WO 98/24499 | 6/1998 |
| | | | | WO | WO 98/26829 | 6/1998 |
| AU | A 32914/95 | 2/1996 | | WO | WO 98/26830 | 6/1998 |
| AU | 9459430 | 2/1996 | | WO | WO 98/48878 | 11/1998 |
| AU | A 41018/97 | 4/1998 | | | | |
| AU | A 89312/98 | 1/1999 | | | | |
| CA | 1039144 | 9/1978 | | | | |
| DE | 459104 | 4/1928 | | | | |
| DE | 701 690 | 1/1941 | | | | |
| DE | 159396 | 6/1981 | | | | |
| DE | 3015279 A1 | 10/1981 | | | | |
| DE | 3345067 A1 | 6/1984 | | | | |
| DE | 3537507 A1 | 4/1987 | | | | |
| DE | 3539073 A1 | 5/1987 | | | | |
| DE | 4004157 C1 | 4/1991 | | | | |
| DE | 4343205 A1 | 6/1995 | | | | |
| DE | 195 48 380 A1 | 7/1996 | | | | |
| DE | 197 35 359 | 1/1998 | | | | |
| DE | 297 23 101 | 7/1998 | | | | |
| DE | 298 10846 U1 | 8/1998 | | | | |
| EP | 0 054 154 | 10/1981 | | | | |
| EP | 0 252 052 | 1/1988 | | | | |
| EP | 0 264 772 | 4/1988 | | | | |
| EP | 0 303 090 B1 | 7/1988 | | | | |
| EP | 0 386 605 A1 | 2/1990 | | | | |
| EP | 0 427 474 A2 | 5/1991 | | | | |
| EP | 0 462 701 A1 | 5/1991 | | | | |
| EP | 0 462 701 | 12/1991 | | | | |

OTHER PUBLICATIONS

Mask 3 Photographs, DeVilbiss Healthcare Inc., DeVilbiss Seal–ring and CPAP Mask Kit (medium) Part 73510–669.

Mask 4 Photographs, Respironics, Inc., onarch Mini Mask With Pressure Port, part #572004.Monarch Headgear, Part # 572011.

Mask 5 Photographs, Healthdyne Technologies, Nasal CPAP Mask (medium narrow), part # 702510.

Mask 6 Photographs, Healthdyne Technologies, Soft Series Nasal CPAP Mask, part 3702020.

Mask 7 Photographs, DeVilbiss Healthcare, Inc., Small mask and Seal Rings, part # 73510–668.

Mask 8 Photographs, Rspironics, Inc., Reusable Contour mask (medium), part # 302180.

Mask 9 Photographs, Healthdyne Technologies, Healthdyne Large Headgear.

Mask 10 Photographs, Respironics, inc., Soft cap (medium), Part #302142.

Mask 11 Photographs, Weinmann: Hamburg, Nasalmaskensystem Mit Schalldämpfer (medium), Part # WN 23105.

Mask 12 Photographs, Life Care.

Mask 13 Photographs, Healthdyne Technologies.

Mask 14, King System.

Mask 15 Photographs, Respironics, Inc., Paediatric Mask.

Mask 16 Photographs, Hans Rudolph Inc., Hans Rudolph Silicone Rubber Face Mask/8900.

Instruction for Use for the Comfort Flap Small Child Contour Nasal Mask Accessory, Respironics Inc., Jul. 19, 1993, 2 pages.

"Comfort Flap™ Improves the Seal on Reusable Contour Nasal Masks," InterVENTions, vol. 3, No. 1, Mar., 1993, 2 pages.

"Order" from *Respironics, Inc. v. ResCare Limited et al.* case, Civil Action No. 95–151, with Exhibits E and G related to information allegedly available before Jul. 26, 1995, 20 pages.

Respironics, Inc. "Nasal Mask and Accessories Guide," Dec. 23, 1991, 6 pages.

"InterVENTions, A Ventilatory Care Newsletter," vol. 93, No. 1, Mar. 1993, Respironics, Inc., 16 pages.

* cited by examiner

NASAL MASK CUSHION ASSEMBLY

This is a continuation of application Ser. No. 08/791,212, filed Jan. 31, 1997, now U.S. Pat. No. 6,112,746.

FIELD OF THE INVENTION

The invention relates generally to a nasal mask and to a cushion therefor, for example, for use in the treatment of respiratory conditions and in assisted respiration.

BACKGROUND OF THE INVENTION

Nasal masks are commonly used in the treatment of respiratory conditions and sleep disorders (e.g., obstructive sleep apnea) by delivering a flow of breathable gas for, or to assist patient respiration. These nasal masks typically receive a gas supply line which delivers gas into a chamber formed by walls of the mask. The walls usually are semi-rigid and have a face contacting portion including an aperture which is aligned with the wearer's nostrils. The face contacting portion can comprise a soft, resilient elastomeric material which may conform to various facial contours. The mask normally is secured to the wearer's head by straps. The straps are adjusted to pull the mask against the face with sufficient force to achieve a gas tight seal between the mask and the wearer's face. Gas is thus delivered to the mask and through the aperture to the wearer's nasal passages.

Problems often arise with masks of the above configuration. For example, the mask may be dislodged, thereby breaking the seal between the mask and wearer. This may occur if the wearer rolls over when sleeping thereby creating a drag force on the gas supply line which is transmitted to the mask, breaking the seal. In the case of a mask being used for the administration of Continuous Positive Airway Pressure (CPAP) treatment for the condition obstructive sleep apnea, such a leak can result in the pressure supplied to the entrance of the wearer's airway being below the therapeutic value, and the treatment becoming ineffective.

Another problem is that the face contacting portion may apply excessive pressure to the wearer's face resulting in discomfort and possibly skin irritation. This can occur because the face contacting portion has to distort beyond its normal range of elasticity to conform to certain facial contours which requires the application of excessive forces. In some cases these excessive pressures and forces may cause the face to distort to conform with the face contacting portion to increase wearer discomfort, facial soreness and ulceration.

Other types of devices exist whereby small nostril nose-pieces (pillows) are held in place by a harness strapped over the wearer's head, for example as shown in prior art U.S. Pat. No. 4,782,832 (Trimble et al). While this arrangement may alleviate some problems regarding seal breakage and skin abrasion, the harnesses associated with such devices are quite cumbersome for the wearer, as are the gas supply lines. Also, air 'jetting' into the nostrils can be irritating to the patient making such devices generally uncomfortable to use.

A further example of the prior art also is disclosed in U.S. Pat. No. 5,243,971 (Sullivan et al).

Cushion masks have also been developed. These cushion masks have an inflated cushion which provides comfort to the wearer. However, these masks, under certain circumstances, may form a tuck or pucker resulting in a leak.

It is an object of the invention to overcome or at least substantially ameliorate one or more of the foregoing disadvantages.

SUMMARY OF THE INVENTION

In one broad form, the invention discloses a nasal mask cushion to sealingly connect a mask to a wearer's face, the cushion comprising:
  a substantially triangularly-shaped frame of resilient material having a rim to surround wearer's nose;
  a membrane also of resilient material, said membrane being relatively more flexible then said frame, and being of the same general shape as said rim and fixed to and extending away from said frame so as to have an outer surface spaced from said rim, a portion of said outer surface forming a face contacting seal; and
  a nose-receiving cavity bounded by said frame and said membrane;
  and wherein said seal portion is generally coterminous with respect to said rim and is resilient deformable towards said rim in use of said cushion.

In one particularly advantageous form, the membrane is substantially saddle-shaped. The membrane further has a centrally located aperture through which the wearer's nose passes to enter said cavity.

It is preferred that the cushion and membrane each include a co-located notch to accommodate the bridge of the nose of the wearer. Typically, the seal portion contacts at least the wearer's nose, and preferably, also the facial tissue around the sides and over the bridge of the nose and between the base of the nose and the top lip.

The invention further discloses a nasal mask for connection to a wearer's face comprising:
  a mask body for connection with supply of breathable gas; and
  a nasal cushion, the body and cushion defining a nose-receiving cavity, said cushion including:
    a substantially triangularly-shaped frame of resilient material having a rim to surround said wearer's nose;
    a membrane also of resilient material, said membrane being relatively more flexible than said frame, and being of the same general shape as said rim and fixed to and extending away from said frame so as to have an outer surface spaced from said frame, a portion of said outer surface forming a face contacting seal;
    and wherein said seal portion is generally coterminous with respect to said rim and is resiliently deformable towards said rim in use of said mask.

The mask body can further include attachment points from which securing straps can be attached, and by which the mask can be secured to the wearer's head. The nasal mask can yet further comprise an arm depending from said body from which a further securing strap(s) can be attached.

The invention further discloses nasal CPAP treatment apparatus comprising a flow generator for the supply of gas at a pressure elevated above atmospheric pressure to a gas delivery conduit, the conduit in turn coupled to a nasal mask as described immediately above.

In one particularly preferred form, a supply of gas can be provided to said cavity, said supply of gas assisting, but not solely causing maintenance of a seal by said seal forming portion of said membrane to the face of the wearer in use of the cushion.

Advantageously, the membrane and the rim are substantially shaped to the facial contour, and the membrane does not need to turn in on itself thus contacting the face without folds or creases. With the cushion/mask secured to the wearer's head, the headstraps need only to be tensioned to balance the force due to mask gas pressure that tends to lift the mask off the face. Such relatively lower mask-to face pressure results in greater patient comfort, and a reduction is the likelihood of skin irritation.

BRIEF DESCRIPTION OF THE DRAWINGS

An embodiment of the invention will now be described with reference to the accompanying drawings, in which.

DETAILED DESCRIPTION OF PREFERRED EMBODIMENTS

Figure 1:
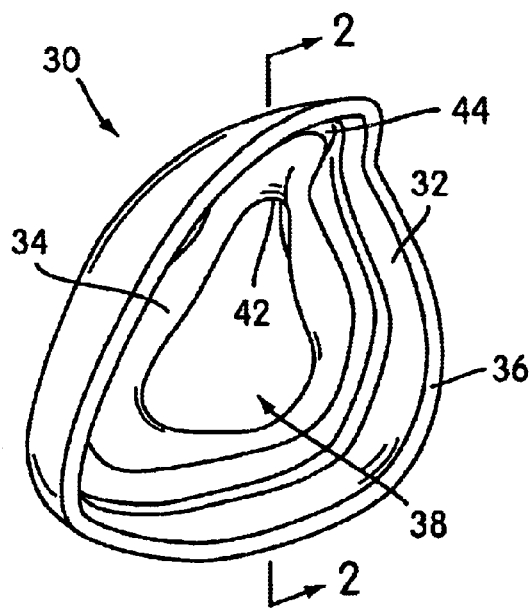
FIG. 1 is a near perspective view of a mask cushion embodying the present invention.
Figure 2:
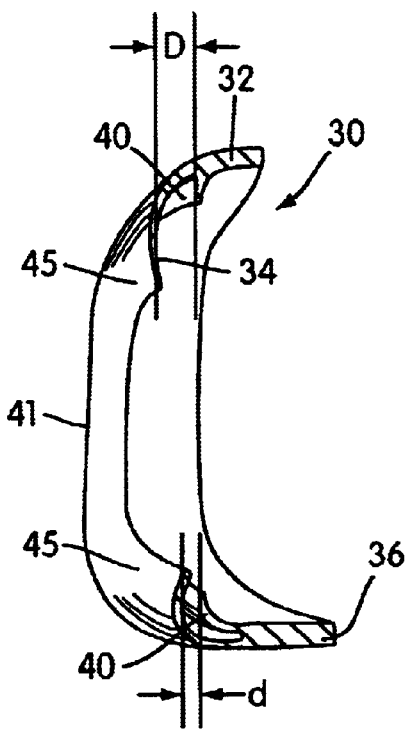
FIG. 2 is a cross-sectional view along line 2—2.

FIG. 1 shows a perspective view of a nasal cushion 30 embodying the invention. FIG. 2 shows the cross-sectional view along line 2—2. Referring to FIGS. 1–2 and 5–9, the cushion 30 comprises a substantially triangularly shaped frame 32 from which extends a membrane 34. The frame 32 has a scalloped edge 36 by which the cushion 30 is affixed to a mask body, as presently will be described.

The membrane 34 has an aperture 38 into which the wearer's nose is received in use of the cushion 30. The membrane 34 is spaced away from the rim 40 of the frame 32, and its outer surface 41 is of substantially the same shape as the rim 40. The outer surface 41 of the membrane 34 and the rim 40 of the frame 32 also can be described as generally saddle shaped. The shaping of the outer surface 41 of the membrane 34 and the rim 40 of the frame 32 also include respective notches 42,44 that receive the bridge of the wearer's nose in use of the cushion 30.

As is best seen in FIG. 2, the frame 32 and the membrane 34 are integrally formed, typically by in a one-shot molding process. The frame 32 and the membrane 34 are fabricated from a resilient material. One suitable such material is SILASTIC™ silicone elastomer manufactured by Dow Corning. The frame 32, in one preferred embodiment, has a typical thickness at its rim 40 of 1.5 mm. The membrane 34, in a preferred embodiment, has a typical thickness of 0.35 mm. In this way, the membrane 34 is relatively more flexible than the rim 40.

In use of the cushion 30, a wearer's nose will be inserted in the aperture 38 to engage a seal forming portion 45 (formed between the dashed lines of FIG. 3) of the outer surface 41 to cause deformation of the membrane 34. Depending upon the securing force supplied to the membrane 34, it may deform to a point where it butts against the rim 40 of the frame 32. The frame 32 has a rigidity sufficient to withstand usual securing pressures in use of the cushion 30 to tend to retain its shape and resist deformation. It thus acts as a supporting structure.

Figure 3:
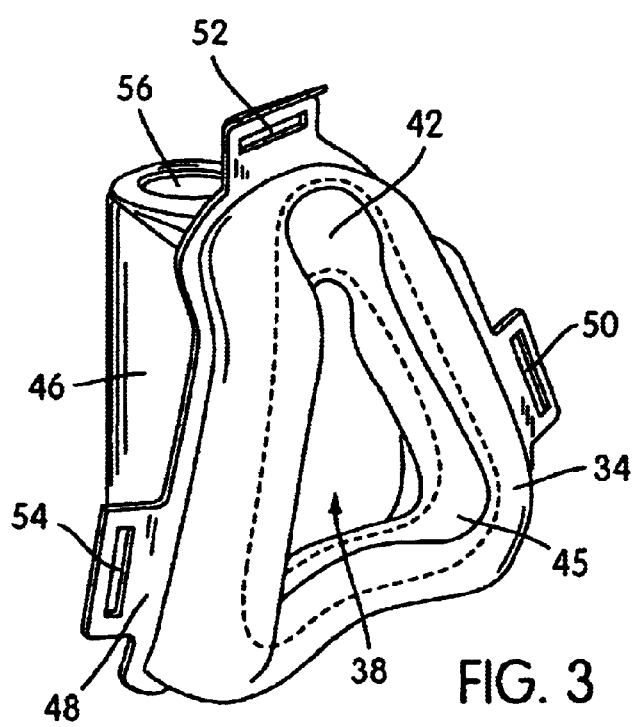
FIG. 3 is a perspective view of a nasal mask including the cushion of FIGS. 1 and 2.

Referring now to FIG. 3, the nasal cushion 30 is shown attached to a mask body 46 by the edge 36 of the frame 32, adhered or otherwise secured to a flange 48 of the mask body 46. Only the outer surface 41 of the membrane 34 can be seen. The flange 48 includes three slots 50, 52, 54 from which tensioning straps can be attached to secure the cushion 30 and the mask body 46 (in combination) to the head of a wearer.

The mask body 46 forms a cavity that can receive the nose of the wearer by the aperture 38. A port 56 is provided at the top of the mask body 46 by which breathable gas can be supplied to the chamber.

Figure 4:
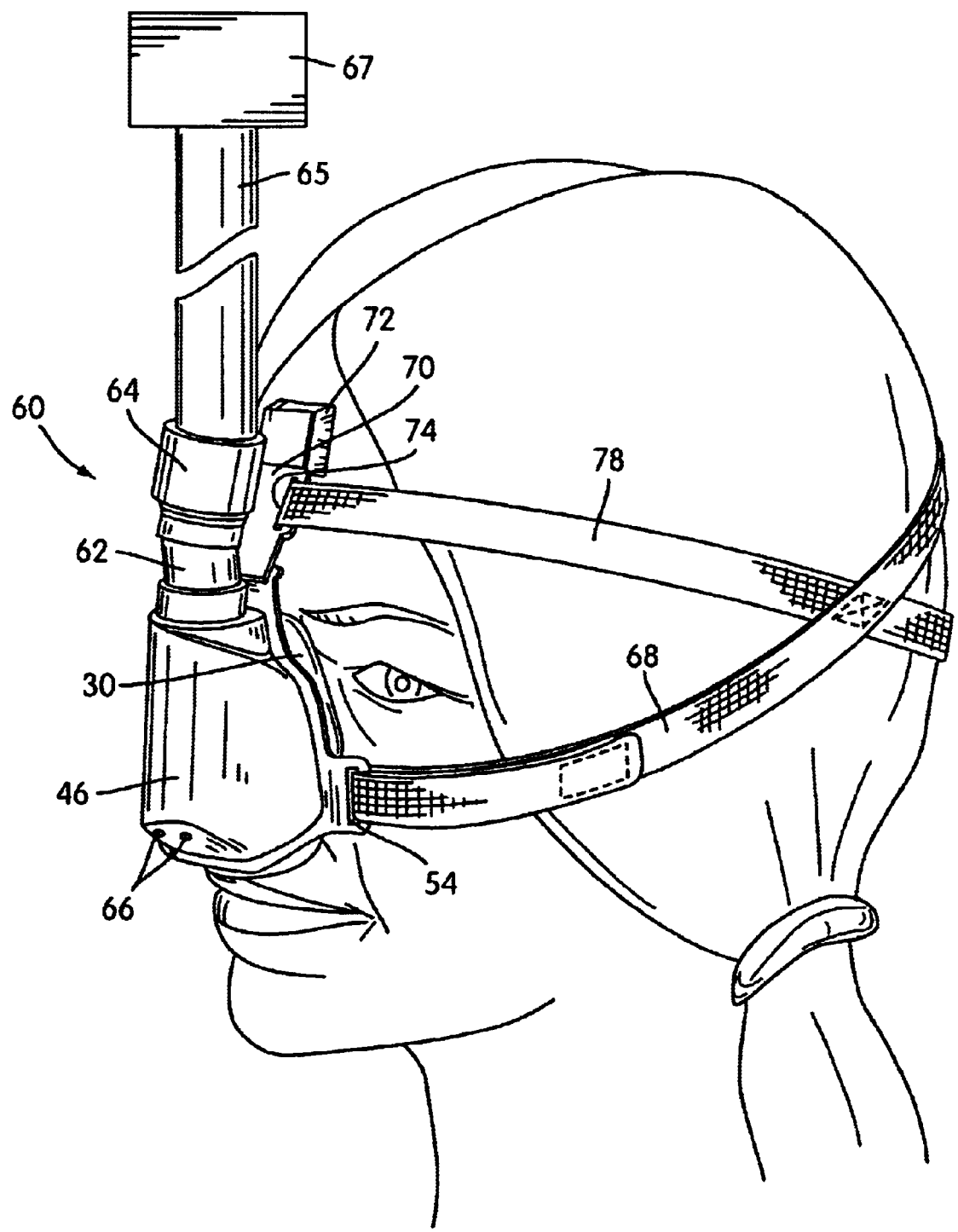
FIG. 4 is a perspective view of the nasal mask of FIG. 3 secured to a wearer's head.
Figure 5:
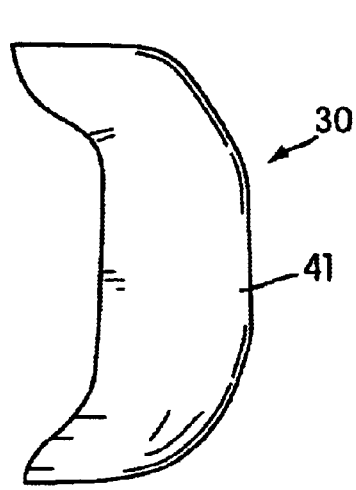
FIG. 5 is a side view of the mask cushion.
Figure 6:
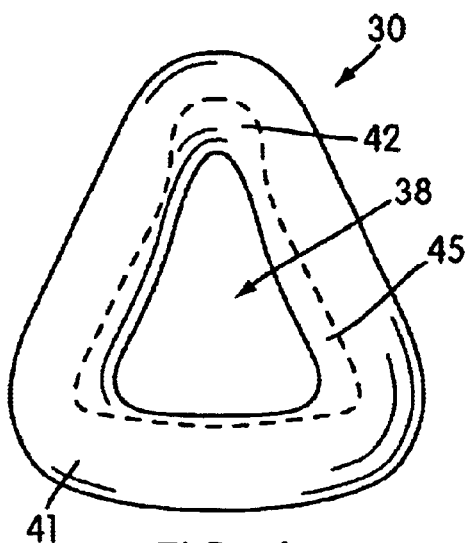
FIG. 6 is a front view of the mask cushion.
Figure 7:
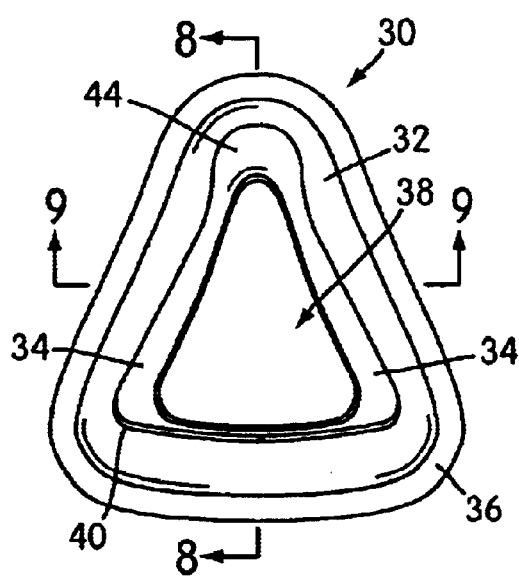
FIG. 7 is a rear view of the mask cushion.
Figure 8:
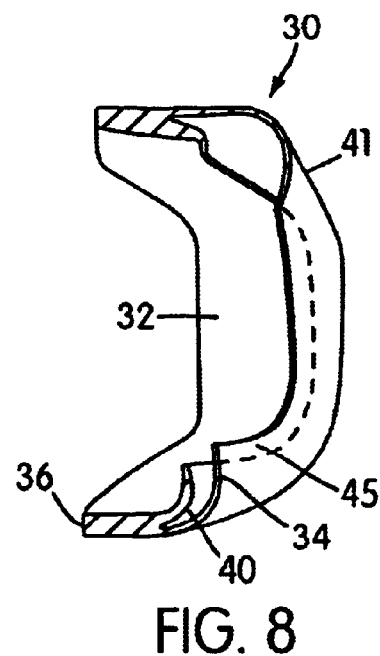
FIG. 8 is a sectional view along section lines 8—8 of FIG. 7.
Figure 9:
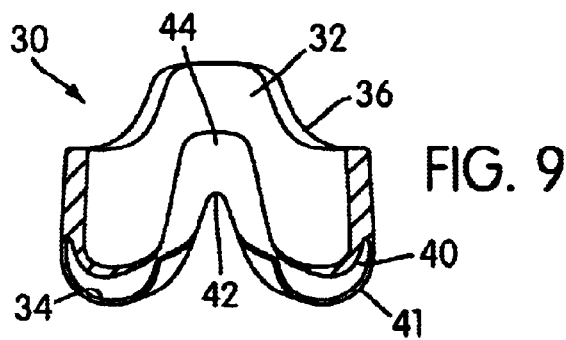
FIG. 9 is a sectional view along section lines 9—9 of FIG. 7.

Referring now to FIG. 4, there is shown a nasal mask 60 including the mask body 46 and the mask cushion 30. A coupling tube 62 is connected at one end with the inlet port 56, and at the other to a socket 64 into which can be received a gas delivery tube 65 for the supply of breathable gas to the chamber internal of the mask body 46. The mask body 46 also has two vent openings 66 by which expired gas is exhausted. A first fastening strap 68 is fixed between to the lower two slots 50, 54. The upper slot 52 receives an arm 70, the top end of which has a resilient pad 72 to engage the forehead of the wearer. The arm 70 has two slots (only one slot shown in FIG. 4) along its side edges, by which a second fastening strap 78 is secured.

In fitting the nasal mask 60, the wearer's nose is received through the aperture 38 into the chamber within the mask body 46. The seal forming portion 45 thus contacts both the surface of the wearer's nose and a portion of the wearer's face in the region between the base of the nose and the upper lip, and around the sides and over the bridge of the nose. The shape of the seal forming portion 45 is particularly suited to effectively seal the difficult region of the facial contour that is the crease between the sides of the nose and the face. Depending upon the tension applied by the fastening straps 68, 78, a seal is formed with the membrane 34 remaining spaced from the rim 40 of the cushion frame 32. While the provision of pressurised gas to the chamber of the mask body 46 assists in the maintenance of a seal between the membrane 34 and the wearer's nose and face, it is not essential in most cases, and an effective seal will be formed absent any such pressurised gas. On relative movement of the mask 60 in relation to the wearer's head, the nose will be restrained by contacting the frame 32. Thus only limited relative motion between the mask 60 and the wearer's nose and face occurs.

The membrane 34 closely imitates the facial contour, and because of its relatively lesser stiffness than the frame 32, can conform to particular facial structures with minimum force, and without a tendency to fold or crease.

If the fastening strap 68,78 are tensioned to excess, the membrane 34 deforms to abut the rim 40 of the cushion 32, the frame 32 thus acting as an "end limit". In such a configuration, almost zero relative movement can occur between the mask 60 and the wearer's head.

FIG. 2 illustrates schematically that, in normal use or before the wearer places the mask on his or her head, a distance d is maintained between the membrane 34 and the frame 36 in the region over the upper lip of the wearer, while a distance D is maintained between the member 34 and the frame 32 in the nasal bridge region of the cushion. The distance D may be larger than the distance d, as shown in FIG. 2.

The nasal cushion 30 and nasal mask 60 has been described with reference to CPAP or assisted respiration treatment, however it is to be understood that the invention generally is applicable to any application where gas and/or atomised liquid is to be supplied to the entrance of the nasal airways. Such applications include nebulisers, gas masks and anaesthetic machines.

We claim:

1. A nasal mask cushion assembly to sealingly connect a nasal mask to a wearer's face by adjusting tension on at least one tension strap connected to the nasal mask, the cushion assembly comprising:
   a generally triangular shaped frame of resilient material, the frame including a nasal bridge region, a lip region, and two cheek regions connecting the nasal bridge and lip regions, the frame also including a rim having an outer surface and a notch in the nasal bridge region; and
   a generally triangularly shaped open ended membrane of resilient material, the membrane including a nasal bridge region, a lip region, and two cheek regions connecting the nasal bridge and lip regions, the membrane also including a longitudinal axis extending generally from the nasal bridge region to the lip region and a generally saddle shaped outer surface, as seen in cross section along the longitudinal axis, adapted to deform and form a seal with the wearer's face when the mask is in use, an inwardly curved rim with an open end spaced from the frame, the inwardly curved rim including an inner surface that opposes and surrounds the rim of the frame, and a notch in the nasal bridge region corresponding to the notch in the nasal bridge region of the frame, wherein
   the inner surface of the inwardly curved rim of the membrane in the nasal bridge region of the membrane is spaced a distance from the outer surface of the rim of the frame in the nasal bridge region of the frame when the mask is not in use;
   the inner surface of the membrane is substantially parallel to the outer surface of the frame in the lip and cheek regions;
   the inner surface of the membrane includes at least one portion that diverges away from the outer surface of the frame in the nasal bridge region, as seen in cross section transverse to the longitudinal axis when the mask is not in use;
   the membrane is more flexible than the frame; and
   the distance between the inner surface of the membrane and the outer surface of the rim of the frame in the nasal bridge region is variable with the tension applied to the at least one tension strap.

2. A nasal mask cushion assembly according to claim 1, wherein the distance varies where the at least one portion of the membrane diverges away from the outer surface of the frame in the nasal bridge region.

3. A nasal mask cushion assembly according to claim 2, wherein the frame and the membrane are formed as an integral, one piece unit.

4. A nasal mask cushion assembly according to claim 1, wherein the frame and the membrane are formed as an integral, one piece unit.

5. A nasal mask cushion assembly according to claim 1, wherein the membrane is formed of silicon.

6. A nasal mask cushion assembly according to claim 5, wherein the membrane is molded.

7. A nasal mask cushion assembly according to claim 6, wherein the lip region of the membrane is adapted to contact an upper lip of the wearer's face.

8. A nasal mask cushion assembly according to claim 7, wherein the membrane is molded to generally match the contours of the wearer's face even when the mask is not in use.

9. A nasal mask cushion assembly according to claim 8, wherein the outer surface of the membrane is substantially the same shape as the rim of the frame at least in the lip and cheek regions.

10. A nasal mask cushion assembly according to claim 9, wherein the outer surface of the membrane and the rim of the frame are convex in relation to the wearer's face.

11. A nasal mask cushion assembly according to claim 10, wherein the rim of the frame is desired to define a maximum deformation position of the membrane in normal use.

12. A nasal mask cushion assembly according to claim 11, wherein the outer surface forms a seal upon connection to the wearer's face and application of a minimum force to the at least one tension strap.

13. A nasal mask cushion assembly according to claim 12, wherein the rim of the flame is an order of magnitude thicker than the membrane.

14. A nasal mask cushion assembly according to claim 13, wherein the rim of the frame is approximately 1.5 mm thick.

15. A nasal mask cushion assembly according to claim 13, wherein the membrane is approximately 0.35 mm thick.

16. A nasal mask cushion assembly according to claim 13, wherein the frame is formed of silicone.

17. A nasal mask cushion assembly according to claim 16, wherein the frame is molded.

18. A nasal mask cushion assembly according to claim 17, wherein the frame and the membrane are formed as a unitary one piece unit.

19. A nasal mask cushion assembly to sealingly connect a nasal mask to a wearer's face by adjusting tension on at least one tension strap connected to the nasal mask, the cushion assembly comprising:
   a generally triangularly shaped frame of resilient material, the frame including an inner surface, an outer surface, an aperture, and a rim defining the perimeter of the aperture, the rim including a notch in a region of the rim adapted to receive the bridge of the wearer's nose; and
   a generally triangularly shaped membrane of resilient material, the membrane including an aperture adapted to receive the wearer's nose, an outer surface including a seal forming portion adapted to deform and form a seal over a portion of the wearer's face in a region between the base of the nose and the upper lip and around the sides and over the bridge of the wearer's nose when the mask is in use, an inner surface opposing the outer surface of the frame and spaced a first distance from the outer surface of the frame in at least the region of the frame adapted to receive the bridge of the wearer's nose when the mask is in use, an edge defining the perimeter of the aperture, and a notch in a region of the membrane adapted to receive the bridge of the wearer's nose, wherein
   the membrane is more flexible than the frame;
   the aperture of the frame is larger than the aperture of the membrane;
   the edge of the membrane is spaced a second distance from the rim, the second distance being variable in the regions of the rim and the membrane adapted to receive the bridge of the wearer's nose; and
   the first distance between the outer surface of the frame and the inner surface of the membrane is variable with the tension applied to the at least one tension strap.

20. A nasal mask cushion assembly according to claim 19, wherein the frame and the membrane are formed in a single piece.

21. A nasal mask cushion assembly according to claim 19, wherein the membrane is formed of silicone.

22. A nasal mask cushion assembly according to claim 21, wherein the membrane is molded.

23. A nasal mask cushion assembly according to claim 22, wherein the membrane is molded to generally match the contours of the wearer's face even when the mask is not in use.

24. A nasal mask cushion assembly according to claim 23, wherein the outer surface of the membrane is substantially the same shape as the rim of the frame in at least a lip and cheek regions of the assembly.

25. A nasal mask cushion assembly according to claim 24, wherein the outer surface of the membrane and the rim of the frame are convex in relation to the wearer's face.

26. A nasal mask cushion assembly according to claim 25, wherein the rim of the frame is designed to define a maximum deformation position of the membrane in normal use.

27. A nasal mask cushion assembly according to claim 26, wherein the outer surface of the membrane forms a seal upon connection to the wearer's face and application of a minimum force to the at least one tension strap.

28. A nasal mask cushion assembly according to claim 27, wherein the rim of the frame is an order of magnitude thicker than the membrane.

29. A nasal mask cushion assembly according to claim 28, wherein the rim of the frame is approximately 1.5 mm thick.

30. A nasal mask cushion assembly according to claim 28, wherein the membrane is approximately 0.35 mm thick.

31. A nasal mask cushion assembly according to claim 27, wherein the frame is formed of silicone.

32. A nasal mask cushion assembly according to claim 31, wherein the frame is molded.

33. A nasal mask cushion assembly according to claim 32, wherein the frame and the membrane are formed as a unitary one piece unit.

34. A nasal mask cushion assembly to sealingly connect a nasal mask to a wearer's face by adjusting tension on at least one tension strap connected to the nasal mask, the cushion assembly comprising:
  a generally triangularly shaped frame of resilient material, the frame including a first side adapted to contact a mask body of the nasal mask, a second side opposite the first side, an aperture extending from the first side to the second side, a rim on the second side extending around the perimeter of the aperture, and a notch in the rim in a region adapted to receive the bridge of the wearer's nose; and
  a generally triangularly shaped membrane of resilient material, the membrane including an aperture adapted to receive the wearer's nose, an edge defining the perimeter of the aperture, a notch in a region adapted to receive the bridge of the wearer's nose, a first surface including a seal forming portion disposed around the perimeter of the aperture adapted to deform and form a seal over a portion of the wearer's face in a region between the base of the nose and the upper lip and around the sides and over the bridge of the wearer's nose when the mask is in use, a second surface opposite the first surface that surrounds and is spaced a first distance from the rim of the frame in at least the region adapted to receive the bridge of the wearer's nose when the mask is in use, wherein
  the membrane is more flexible than the frame;
  the aperture of the membrane is smaller than the aperture of the frame;
  the edge of the membrane is spaced a second distance from the rim of the frame, the second distance being variable in the regions of the membrane and the frame adapted to receive the bridge of the wearer's nose;
  the first distance between the second surface of the membrane and the rim of the frame is variable with the tension applied to the at least one tension strap.

35. A nasal mask cushion assembly according to claim 34, wherein the frame and the membrane are formed in a single piece.

36. A nasal mask cushion assembly according to claim 34, wherein the membrane is formed of silicone.

37. A nasal mask cushion assembly according to claim 36, wherein the membrane is molded.

38. A nasal mask cushion assembly according to claim 37, wherein the membrane is molded to generally match the contours of the wearer's face even when the mask is not in use.

39. A nasal mask cushion assembly according to claim 38, wherein the outer surface of the membrane is substantially the same shape as the rim of the frame in at least a lip and cheek regions of the assembly.

40. A nasal mask cushion assembly according to claim 39, wherein the second surface of the membrane and the rim of the frame are convex in relation to the wearer's face.

41. A nasal mask cushion assembly according to claim 40, wherein the rim of the frame is designed to define a maximum deformation position of the membrane in normal use.

42. A nasal mask cushion assembly according to claim 41, wherein the seal forming portion forms a seal upon connection to the wearer's face and application of a minimum force to the at least one tension strap.

43. A nasal mask cushion assembly according to claim 42, wherein the rim of the frame is at least an order of magnitude thicker than the membrane.

44. A nasal mask cushion assembly according to claim 43, wherein the rim of the frame is approximately 1.5 mm thick.

45. A nasal mask cushion assembly according to claim 43, wherein the membrane is approximately 0.35 mm thick.

46. A nasal mask cushion assembly according to claim 42, wherein the frame is formed of silicone.

47. A nasal mask cushion assembly according to claim 46, wherein the frame is molded.

48. A nasal mask cushion assembly according to claim 47, wherein the frame and the membrane are formed as a unitary one piece unit.

49. A nasal mask for connection to a wearer's face comprising:
  a mask body for connection with a supply of breathable gas; and
  a nasal cushion secured to said mask body, the body and cushion forming a nose-receiving cavity, said cushion including:
    a nasal bridge region, a cheek region and a lip region;
    a substantially triangularly-shaped first membrane of resilient material having a first molded rim that at least partially surrounds a wearer's nose, at least a portion of the first molded rim being inwardly curved; and
    a second membrane also of resilient material, said second membrane having a second molded rim that is inwardly curved, said second molded rim being fixed to and extending away from said first membrane so as to have a second membrane inner surface spaced a distance from an outer surface of said first molded rim, a portion of said second molded rim forming a face contacting seal that is preformed to generally match the facial contours of the wearer;
  wherein said seal portion is substantially coterminous with respect to said second molded rim and is resiliently deformable towards said first membrane in use of said mask, at least a portion of the second molded rim remaining spaced from the first molded rim when the mask is connected to the wearer's face.

50. The nasal mask of claim 49, further comprising an arm coupled to and extending above the nasal bridge region of the mask, the arm including an oblong slot positioned on each lateral side of the arm to receive a strap.

51. The nasal mask of claim 50, further comprising a single resilient pad mounted on the arm and centered above the nasal bridge region of the mask.

52. The nasal mask of claim 49, wherein the second membrane is conformable, in use, to various facial structures with minimum force.

53. The nasal mask of claim 52, wherein a maximum deformation position of the second membrane is defined by the first membrane.

54. The nasal mask of claim 53, wherein the maximum deformation position is not reached under normal tightening force of the mask to the wearer's face.

55. The nasal mask of claim 54, wherein the first and second membranes are formed as a one-piece unit.

56. The nasal mask of claim 55, wherein the first membrane is thicker than the second membrane.

57. A nasal mask according to claim 49, wherein the membrane is formed of silicone.

58. A nasal mask according to claim 57, wherein the lip region of the mask is adapted to contact an upper lip of the wearer's face.

59. A nasal mask according to claim 58, wherein the second membrane is molded to generally match the contours of the wearer's face even when the mask is not in use.

60. A nasal mask according to claim 59, wherein an outer surface of the second membrane is substantially the same shape as the first molded rim of the first membrane in at least the lip and cheek regions.

61. A nasal mask according to claim 60, wherein the second molded rim and the first molded rim are convex in relation to the wearer's face.

62. A nasal mask according to claim 61, wherein the first molded rim of the first membrane is designed to define a maximum deformation position of the second membrane in normal use.

63. A nasal mask according to claim 62, wherein the seal portion forms a seal upon connection to the wearer's face and application of a minimum force to a strap connected to the mask body.

64. A nasal mask according to claim 63, wherein the first molded rim is an order of magnitude thicker than second membrane.

65. A nasal mask according to claim 64, wherein the first molded rim is approximately 1.5 mm thick.

66. A nasal mask according to claim 64, wherein the second membrane is approximately 0.35 mm thick.

67. A nasal mask according to claim 63, wherein the first membrane is formed of silicone.

68. A nasal mask according to claim 67, wherein the first and second membranes are formed as a unitary one piece unit.

69. A cushion and mask assembly comprising:
a mask including a mask shell constructed to receive a supply of breathable air, an arm extending away from the mask shell and including an oblong slot positioned on each lateral side of the arm to receive a strap, and at least one resilient pad mounted on the arm; and
a cushion having a main upstanding wall, the wall having a first end removably coupleable to the mask and a second end defining an opening into a nasal cavity formed by the mask and the cushion, the wall including a first membrane positioned between the first and second ends and extending inwardly onto the nasal cavity, the second end of the wall defining a second membrane being shaped to generally match facial contours of a wearer and so as to form a seal over a portion of the wearer's face in a region between the base of the nose and the upper lip and around the sides and over the bridge of the wearer's nose when the mask is in use, the second membrane being spaced from the first membrane to define a gap having a width that is greater than a thickness of the first membrane, the first membrane having a width that is less than a distance from an intersection of the second membrane and the wall to an edge of the second membrane defining an aperture of the nasal cavity, the second membrane overhanging and covering substantially all portions of the first membrane, the first membrane acting to define a maximum deformation position of the second membrane in use.

70. The cushion and mask assembly of claim 69, wherein the second membrane s conformable, in use, to various facial structures with minimum force.

71. The cushion and mask assembly of claim 70, wherein the first and second membranes are formed as a one-piece unit.

72. The cushion and mask assembly of claim 71, wherein the first membrane is thicker than the second membrane.

73. A cushion and mask assembly according to claim 69, wherein the second membrane is formed of silicone.

74. A cushion and mask assembly according to claim 73, wherein the second membrane is molded.

75. A cushion and mask assembly according to claim 74, wherein the second membrane is substantially the same shape as the first membrane in at least a lip and cheek regions of the assembly.

76. A cushion and mask assembly according to claim 75, wherein the first and second membranes are convex in relation to the wearer's face.

77. A cushion and mask assembly according to claim 76, wherein the second membrane forms a seal upon connection to the wearer's face and application of a minimum force to the strap.

78. A cushion and mask assembly according to claim 77, wherein the first membrane is an order of magnitude thicker than the second membrane.

79. A cushion and mask assembly according to claim 78, wherein the first membrane is approximately 1.5 mm thick.

80. A cushion and mask assembly according to claim 78, wherein the second membrane is approximately 0.35 mm thick.

81. A cushion and mask assembly according to claim 77, wherein the first membrane is formed of silicone.

82. A cushion and mask assembly according to claim 81, wherein the first membrane is molded.

83. A cushion and mask assembly according to claim 82, wherein the first and second membranes are formed as a unitary one piece unit.

84. A nasal mask cushion to sealingly connect a mask to a wearer's face, the cushion comprising:
a nasal bridge region, a cheek region and a lip region;
a first membrane comprising a substantially triangularly-shaped frame of resilient material having a first molded rim of said first membrane; and
a second membrane of resilient material, said second membrane being thinner than said first membrane, said second membrane having a second molded rim that is inwardly curved, said second rim spaced a first distance from said first rim in said lip region and said second rim spaced a second distance from said first rim in said nasal bridge region, said second distance greater than said first distance, said distances measured when the mask is not in use, a portion of said second membrane curved rim forming a face contacting seal.

85. A nasal cushion as claimed in claim 84, wherein said second molded rim and said first molded rim have a co-located notch to accommodate the bridge of a wearer's nose.

86. A nasal cushion as claimed in claim 85, wherein said first molded rim and said second molded rim are substantially saddle-shaped.

87. A nasal cushion as claimed in claim 86, wherein said second membrane is shaped so that said seal portion, in use, contacts at least a wearer's nose.

88. A nasal cushion as claimed in claim 87, wherein said seal portion, in use, contacts the facial tissue around the sides and over the bridge of the nose, and between the base of the nose and the top lip.

89. A nasal cushion as claimed in claim 88, wherein said second rim and seal portion are shaped to generally match facial contours in the region of facial tissue around the sides and over the bridge of the nose, and between the base of the nose and top lip.

90. The nasal mask cushion of claim 87, wherein the first and second membranes comprise one molded piece, without being adhered together by an adhesive.

91. The nasal mask cushion of claim 90, wherein the first molded inwardly curved rim of said first membrane is approximately 1.5 mm thick.

92. The nasal mask cushion of claim 91, wherein the second molded inwardly curved rim of the second membrane is approximately 0.35 mm thick.

93. A nasal mask cushion according to claim 84, wherein the second membrane is formed of silicone.

94. A nasal mask cushion according to claim 93, wherein the lip region is adapted to contact an upper lip of the wearer's face.

95. A nasal mask cushion according to claim 94, wherein the second membrane is molded to generally watch the contours of the wearer's face even when the mask is not in use.

96. A nasal mask cushion according to claim 95, wherein an outer surface of the second membrane is substantially the same shape as the first molded rim of the first membrane.

97. A nasal mask cushion according to claim 96, wherein the outer surface of the second membrane and the first molded rim of the frame are convex in relation to the wearer's face.

98. A nasal mask cushion according to claim 97, wherein the first molded rim is designed to define a maximum deformation position of the second membrane in normal use.

99. A nasal mask cushion according to claim 98, wherein the seal portion forms a seal upon connection to the wearer's face and application of a minimum force to a swap connected to the mask.

100. A nasal mask cushion according to claim 99, wherein the first molded run is an order of magnitude thicker than the second membrane.

101. A nasal mask cushion according to claim 100, wherein the first molded rim of the frame is approximately 1.5 mm thick.

102. A nasal mask cushion according to claim 100, wherein the second membrane is approximately 0.35 mm thick.

103. A nasal mask cushion according to claim 99, wherein the first membrane is formed of silicone.

104. A nasal mask cushion according to claim 103, wherein the first membrane and the second membrane are formed as a unitary one piece unit.

105. A nasal mask cushion assembly to sealingly connect a nasal mask to a wearer's face by adjusting tension on at least one tension strap connected to the nasal mask, the cushion assembly comprising:

a generally triangular shaped frame of resilient material, the frame including a nasal bridge region, a lip region, and two cheek regions connecting the nasal bridge and lip regions, the frame also including a rim having an outer surface; and a generally triangularly shaped open ended membrane of resilient material, the membrane including a nasal bridge region, a lip region, and two cheek regions connecting the nasal bridge and lip regions, the membrane also including a longitudinal axis extending generally from the nasal bridge region to the lip region and an outer surface adapted to deform and form a seal with the wearer's face when the mask is in use, an inwardly curved rim with an open end spaced from the frame, the inwardly curved rim including an inner surface that opposes and surrounds the rim of the frame, and a notch in the nasal bridge region, wherein the inner surface of the inwardly curved rim of the membrane in the nasal bridge region of the membrane is spaced a distance from the frame in the nasal bridge region of the frame when the mask is not in use;

the inner surface of the membrane is substantially parallel to the outer surface of the frame in the lip and check regions;

the inner surface of the membrane includes at least one portion that diverges away from the frame in the nasal bridge region, as seen in cross section transverse to the longitudinal axis when the mask is not in use;

the membrane is more flexible than the frame; and the distance between the inner surface of the membrane and the frame in the nasal bridge region is variable with the tension applied to the at least one tension strap.

106. A nasal mask cushion assembly according to claim 105, wherein the membrane is formed of silicone.

107. A nasal mask cushion assembly according to claim 106, wherein the membrane is molded.

108. A nasal mask cushion assembly according to claim 107, wherein the lip region of the membrane is adapted to contact an upper lip of the wearer's face.

109. A nasal mask cushion assembly according to claim 108, wherein the membrane is molded to generally match to contours of the wearer's face even when the mask is not in use.

110. A nasal mask cushion assembly according to claim 109, wherein the distance varies where the at least one portion of the membrane diverges away from the outer surface of the frame in the nasal bridge region.

111. A nasal mask cushion assembly according to claim 110, wherein an edge of the inwardly curved rim of the membrane is spaced a second distance from the rim of the frame.

112. A nasal mask cushion assembly according to claim 111, wherein the second distance varies.

113. A nasal mask cushion assembly according to claim 112, wherein the outer surface of the membrane is substantially the same shape as the rim of the frame at least in the lip and cheek regions.

114. A nasal mask cushion assembly according to claim 113, wherein the outer surface of the membrane and the rim of the frame are convex in relation to the wearer's face.

115. A nasal mask cushion assembly according to claim 114, wherein the rim of the frame is designed to define a maximum deformation position of the membrane in normal use.

116. A nasal mask cushion assembly according to claim 115, wherein the outer surface forms a seal upon connection to the wearer's face and application of a minimum force to the least one tension strap.

117. A nasal mask cushion assembly according to claim 116, wherein the rim of the frame is an order of magnitude thicker than the membrane.

118. A nasal mask cushion assembly according to claim 117, wherein the rim of the frame is approximately 1.5 mm thick.

119. A nasal mask cushion assembly according to claim 117, wherein the membrane is approximately 0.35 mm thick.

120. A nasal mask cushion assembly according to claim 116, wherein the frame is molded.

121. A nasal mask cushion assembly according to claim 120, wherein the frame is formed of silicone.

122. A nasal mask cushion assembly according to claim 121, wherein the frame and the membrane are formed as a unitary one piece unit.

123. A nasal mask for connection to a wearer's face, comprising:
    a mask body for connection with a supply of breathable gas; and
    a nasal cushion secured to said mask body, the mask body and cushion forming a nose-receiving cavity, said cushion including:
        a nasal bridge region, a cheek region and an upper lip region;
        a substantially triangularly-shaped inner support member of resilient material having a first surface that at least partially surrounds a wearer's nose, at least a portion of the first surface being inwardly curved, and a notch in the nasal bridge region; and
        an outer membrane also of resilient material, said outer membrane having a rim that is inwardly curved and a notch in the nasal bridge region aligned with the notch in the inner support member, said rim being structured so as to have an inner surface at least a portion of which is spaced from said first surface of said inner support member in at least the upper lip region when the mask is not in use, a portion of said rim forming a seal portion, wherein:
            said seal portion is substantially coterminous with respect to said rim and is resiliently deformable towards said inner support member in use of said mask,
            the outer membrane is molded of silicone,
            the outer membrane is preformed to generally match the contours of the wearer's face even when the mask is not in use, and
            the rim of the outer membrane and the first surface of the inner support member are convex in relation to the wearer's face.

124. A nasal mask according to claim 123, wherein the inner surface of the outer membrane is spaced from the first surface of the inner support member in at least a portion of the cheek region as well as the upper lip region.

125. A nasal mask according to claim 124, wherein the first surface of the inner support member is designed to define a maximum deformation position of the outer membrane in normal use.

126. A nasal mask according to claim 125, wherein the outer membrane is more flexible than the inner support member.

127. A nasal mask according to claim 125, wherein the seal portion forms a seal upon connection to the wearer's face and application of a minimum force to a strap connected to the mask body.

128. A nasal mask according to claim 127, wherein the first surface of the inner support member is an order of magnitude thicker than the rim of the outer membrane.

129. A nasal mask according to claim 123, wherein the inner support member and the outer membrane are formed as a single piece.

130. A nasal mask according to claim 123, wherein at least a portion of the rim of the outer membrane is structured to remain spaced from the first surface of the inner support member when the mask is connected to the wearer's face.

* * * * *